US007077965B2

(12) United States Patent
Williamson et al.

(10) Patent No.: US 7,077,965 B2
(45) Date of Patent: Jul. 18, 2006

(54) FLUID TREATMENT SYSTEM

(75) Inventors: Christian Williamson, Tuscon, AZ (US); Douglas Penhale, London (CA); Scott Roger, London (CA)

(73) Assignee: Trojan Technologies Inc. (CA)

( * ) Notice: Subject to any disclaimer, the term of this patent is extended or adjusted under 35 U.S.C. 154(b) by 1 day.

(21) Appl. No.: 10/247,317

(22) Filed: Sep. 20, 2002

(65) Prior Publication Data

US 2003/0080071 A1    May 1, 2003

Related U.S. Application Data

(60) Provisional application No. 60/323,383, filed on Sep. 20, 2001.

(51) Int. Cl.
*C02F 1/32* (2006.01)
(52) U.S. Cl. ............... 210/748; 210/252; 210/262; 210/241; 422/189
(58) Field of Classification Search ........... 210/748, 210/252, 262, 241, 192, 198.1, 512.2; 96/224; 55/315, 342; 422/186.3, 189, 24, 121, 170; 204/409, 666; 250/437, 438
See application file for complete search history.

(56) References Cited

U.S. PATENT DOCUMENTS

| | | | | |
|---|---|---|---|---|
| 2,663,561 A | * | 12/1953 | Muller | ............... 432/58 |
| 4,482,809 A | * | 11/1984 | Maarschalkerweerd | ..... 250/436 |
| 4,767,932 A | * | 8/1988 | Ellner | ............... 250/435 |
| 4,872,980 A | * | 10/1989 | Maarschalkerweerd | ..... 210/243 |
| 5,006,244 A | * | 4/1991 | Maarschalkerweerd | ..... 210/243 |
| 5,141,636 A | | 8/1992 | Flanagan et al. | ........... 210/209 |
| 5,227,140 A | * | 7/1993 | Hager et al. | ........... 422/186.3 |
| 5,401,474 A | | 3/1995 | Hager et al. | |
| 5,504,335 A | * | 4/1996 | Maarschalkerweerd | ..... 250/435 |
| 5,772,901 A | * | 6/1998 | Yu et al. | ............... 210/806 |
| RE36,896 E | * | 10/2000 | Maarschalkerweerd | .. 422/186.3 |
| 6,659,431 B1 | * | 12/2003 | Fang et al. | ............... 250/431 |
| 6,683,313 B1 | * | 1/2004 | Chen et al. | ........... 250/455.11 |

FOREIGN PATENT DOCUMENTS

| DE | 195 43 503 | 5/1997 |
|---|---|---|
| WO | WO 00 20045 | 4/2000 |

* cited by examiner

*Primary Examiner*—Duane Smith
*Assistant Examiner*—Douglas J. Theisen
(74) *Attorney, Agent, or Firm*—Katten Muchin Rosenman LLP (57) ABSTRACT

There is described a fluid treatment system comprising an array of independent fluid treatment reactors. The reactors are arranged in a manner whereby a flow of fluid may be passed through the array in a substantially helical direction. The fluid treatment system is capable of treating large volumes of fluid (e.g., water) while requiring a relatively small foot print. In essence, the present fluid treatment system concentrates a relatively large number of radiation sources in a relatively small amount of space resulting in the ability to treat large volumes of fluid (e.g., water).

117 Claims, 5 Drawing Sheets

FLUID TREATMENT SYSTEM

CROSS-REFERENCE TO RELATED APPLICATION

The present application claims the benefit under 35 U.S.C. §119(e) of provisional patent application Ser. No. 60/323,383, filed Sep. 20, 2001, the contents of which are hereby incorporated by reference.

BACKGROUND OF THE INVENTION

1. Field of the Invention

In one of its aspects, the present invention relates to a fluid treatment system. In another of its aspects, the present invention relates to a method of treating fluid.

2. Description of the Prior Art

Fluid treatment devices and systems are known. For example, U.S. Pat. Nos. 4,482,809, 4,872,980, 5,006,244 and U.S. Re. Pat. No. 36,896 (all assigned to the assignee of the present invention) all describe gravity fed fluid treatment systems which employ ultraviolet (UV) radiation to inactivate microorganisms present in the fluid.

The devices and systems described in the 809, 980 and 244 patents generally include several UV lamps each of which are mounted within sleeves extending between two support arms of the frames. The frames are immersed into the fluid to be treated which is then irradiated as required. The amount of radiation to which the fluid is exposed is determined by the proximity of the fluid to the lamps. One or more UV sensors may be employed to monitor the UV output of the lamps and the fluid level is typically controlled, to some extent, downstream of the treatment device by means of level gates or the like.

The system described in the 896 patent is a significant advance in the art in that it obviates a number of disadvantages deriving from the devices and systems 809, 980 and 244 patents. Unfortunately, the system described in the 896 patent is ideally suited for use in an open, channel-like system and is not readily adaptable to be used in a completely closed system where the flow of fluid is fed under pressure in a pipe.

Closed fluid treatment devices are known—see, for example, U.S. Pat. No. 5,504,335 (assigned to the assignee of the present invention). The 335 patent teaches a closed fluid treatment device comprising a housing for receiving a flow of fluid. The housing comprises a fluid inlet, a fluid outlet, a fluid treatment zone disposed between the fluid inlet and the fluid outlet, and at least one radiation source module disposed in the fluid treatment zone. The fluid inlet, the fluid outlet and the fluid treatment zone are in a collinear relationship with respect to one another. The at least one radiation source module comprises a radiation source sealably connected to a leg which is sealably mounted to the housing. The radiation source is disposed substantially parallel to the flow of fluid. The radiation source module is removable through an aperture provided in the housing intermediate to fluid inlet and the fluid outlet thereby obviating the need to physically remove the device for service of the radiation source.

While the closed fluid treatment device taught in the 335 patent (including the prior art device referred to in that patent) has been commercially successful to some degree, there is still room for improvement in the art.

Specifically, in many installations where it is desirable to treat large amounts of fluid (e.g., water), there is insufficient room to utilize a device such as that described in the 809, 980, 244 and 896 patents. Further, devices such as those taught in the 335 patent are constrained by the volume of fluid (e.g., water) which they can adequately treat (e.g., to subject the fluid to a radiation dose sufficient to perform the desired treatment).

Accordingly, there remains a need in the art for a fluid treatment system which combines the capacity of fluid volume treatment of the 809, 980, 244 and 896 patents while requiring a space of "foot print" not much larger than that used in the device taught by the 335 patent.

SUMMARY OF THE INVENTION

It is an object of the present invention to obviate or mitigate at least one of the above-mentioned disadvantages of the prior art.

Accordingly, in one of its aspects, the present invention provides a fluid treatment system comprising an array of independent fluid treatment reactors arranged in a manner whereby a flow of fluid may be passed through the array in a substantially helical direction.

In another of its aspects, the present invention provides a method of treating fluid comprising the steps of feeding fluid to be treated through an array of independent fluid treatment reactors arranged in a substantially helical direction.

Thus, the present inventors have developed a fluid treatment system which is capable of treating large volumes of fluid (e.g., water) while requiring a relatively small foot print. In essence, the present fluid treatment system concentrates a relatively large number of radiation sources in a relatively small amount of space resulting in the ability to treat large volumes of fluid (e.g., water).

While the present invention relates to fluid treatment devices generally, the most preferred application of the system is in treating liquids such as water (e.g., municipal waste water, drinking water, contaminated ground water, industrial waste water and the like). However, those with skill in the art will recognize that the present fluid treatment system will also find utility in treating other types of fluids such as gases and the like.

The currently preferred embodiment of the present fluid treatment system comprises helical arrangement of interconnected fluid treatment subsystems or "reactors". While the number of reactors is not specifically restricted, in a preferred embodiment, there are nine reactors arranged in rows of the three reactors with three such rows in a stacked arrangement. With this preferred arrangement, it is possible to implement an overall treatment system which comprises, for example from about 250 to about 650 amalgam radiation lamps in a footprint of about 250 square feet, inclusive of all hardware (including virtually all hardware for the system such as reactors, ballasts and the like). The number of reactors in each row of the helical pattern is not particularly restricted. Preferably, each row in the helical pattern comprises at least 3 reactors, preferably from 3 to 6 reactors, per row of the helical pattern. Further the number of rows of reactors in the helical pattern is not particularly restricted. Preferably, the helical pattern comprises at least 2, preferably from 2 to 10, rows of interconnected reactors.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Thus, with reference to FIGS. 1–4, there is illustrated a fluid treatment system 100. Fluid treatment system 100 comprises a fluid treatment system reactor array 105 and a master control panel 110 which is remote from fluid treatment reactor array 105.

Fluid treatment reactor array 105 comprises an inlet 115 and an outlet 120. Fluid treatment reactor array 105 further comprises a skid 125. Fluid treatment reactor array 105 further comprises a trio of power control panels 130,135, 140.

Skid 125 comprises a grid-like series of vertical supports 145 which are interconnected to a series of horizontal supports 150.

The network of vertical supports 145 and horizontal supports 150 provides a support system for nine radiation reactors 155. The design of each reactor 155 is the same and will be described in more detail below.

As shown in FIGS. 1–4, the radiation reactors are stacked in rows of three on top of one another. This arrangement is facilitated through the use of elbows 160 as needed.

Figure 1:
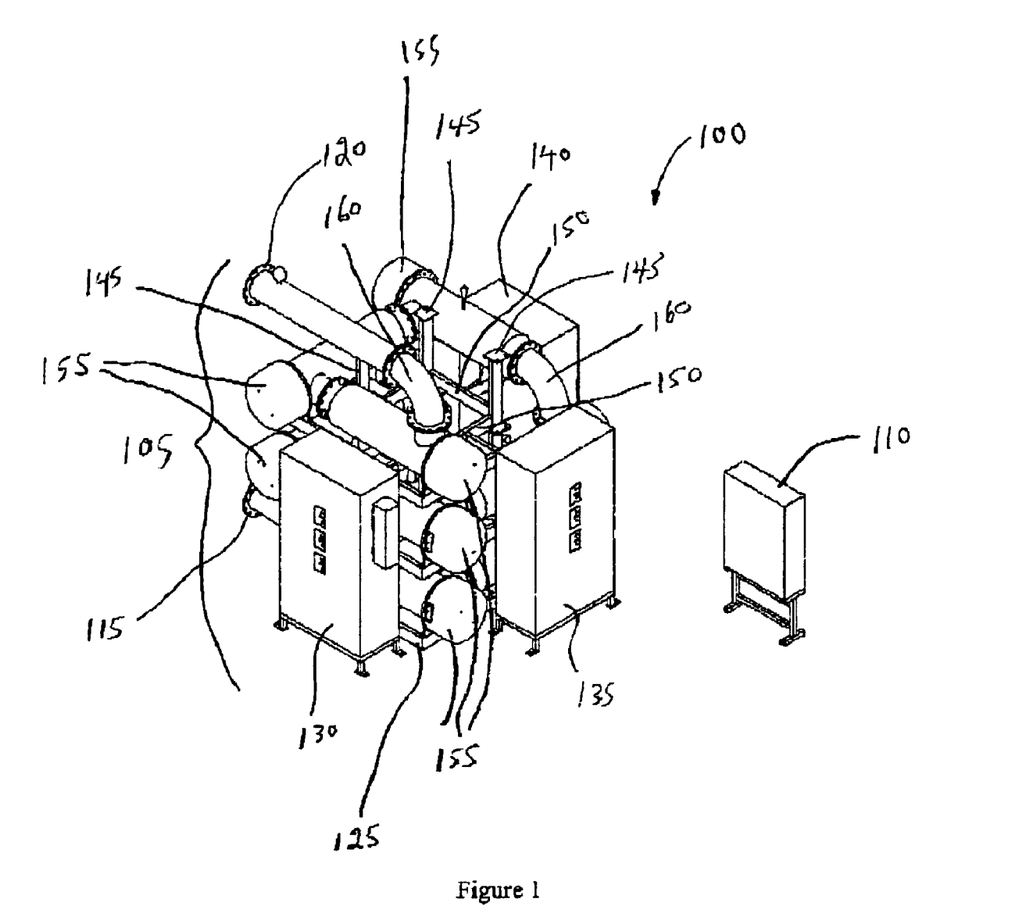
FIG. 1 illustrates a perspective view of a preferred embodiment of the present fluid treatments system.
Figure 2:
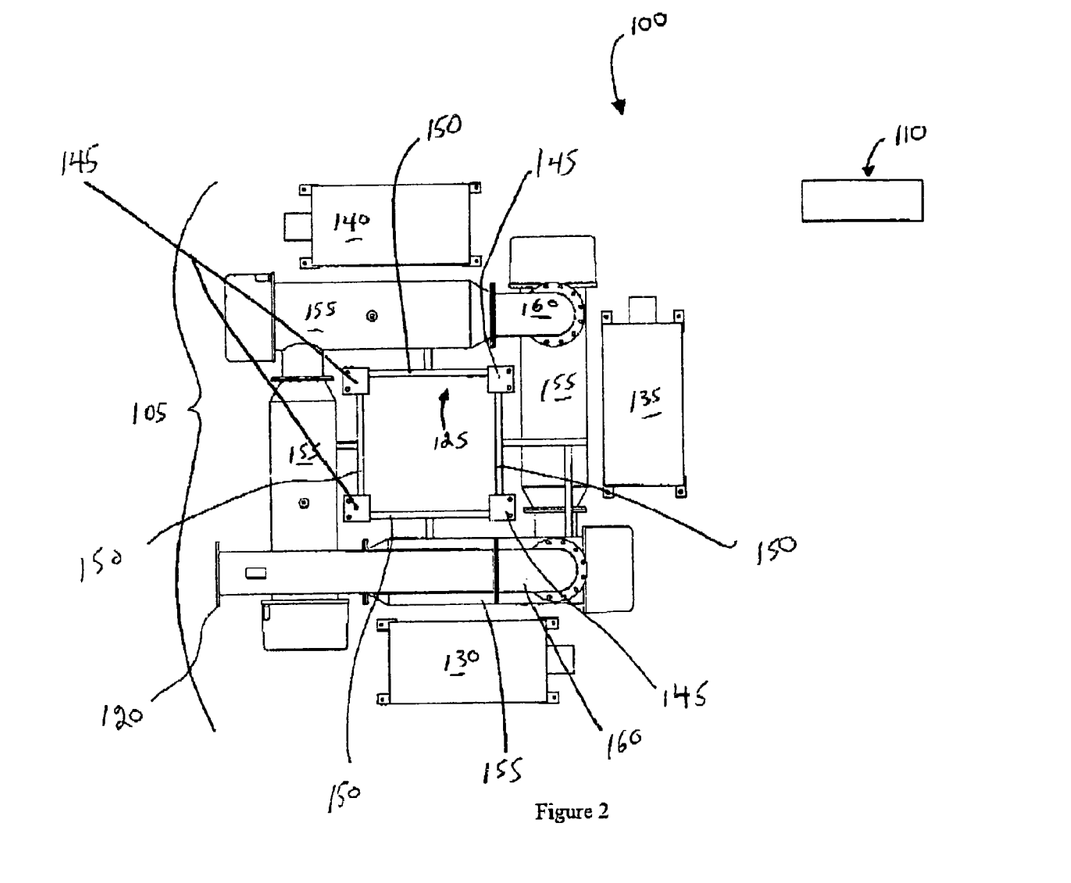
FIG. 2 illustrates a top view of the system illustrated in FIG. 1.
Figure 3:
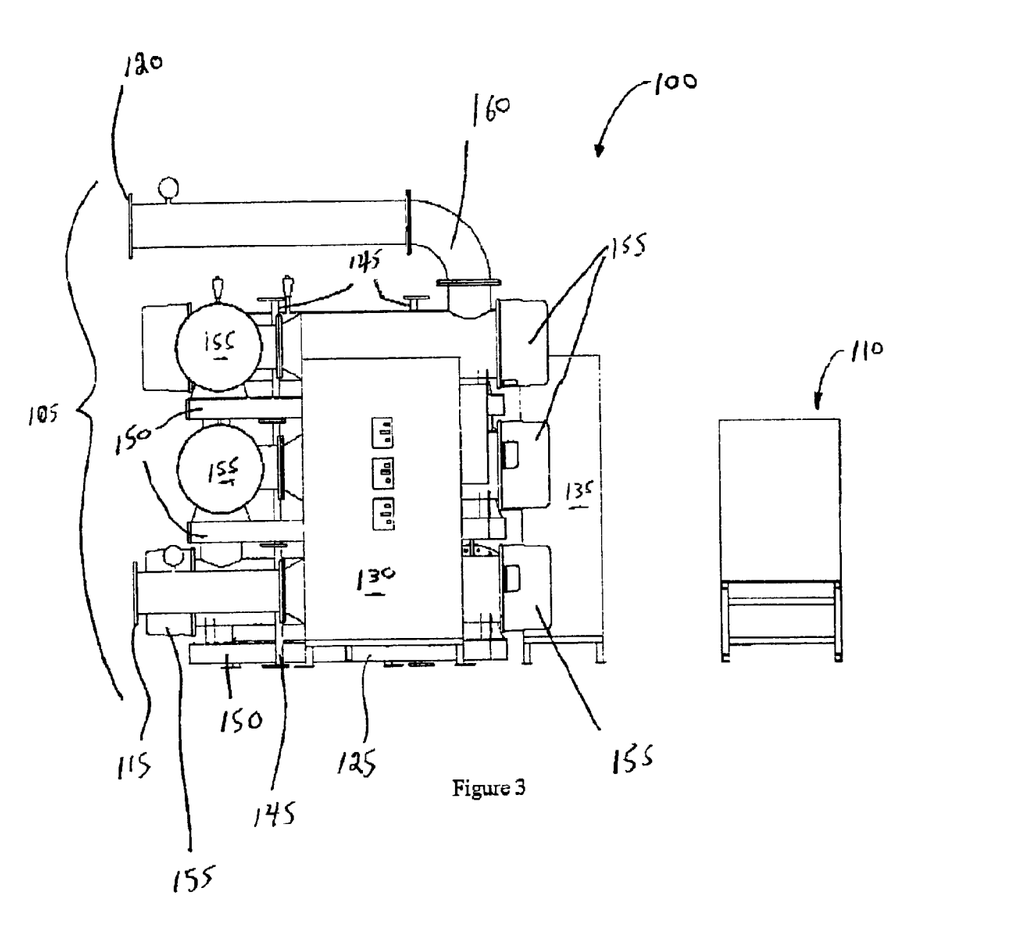
FIG. 3 illustrates a first side elevation of the system illustrated in FIG. 1.
Figure 4:
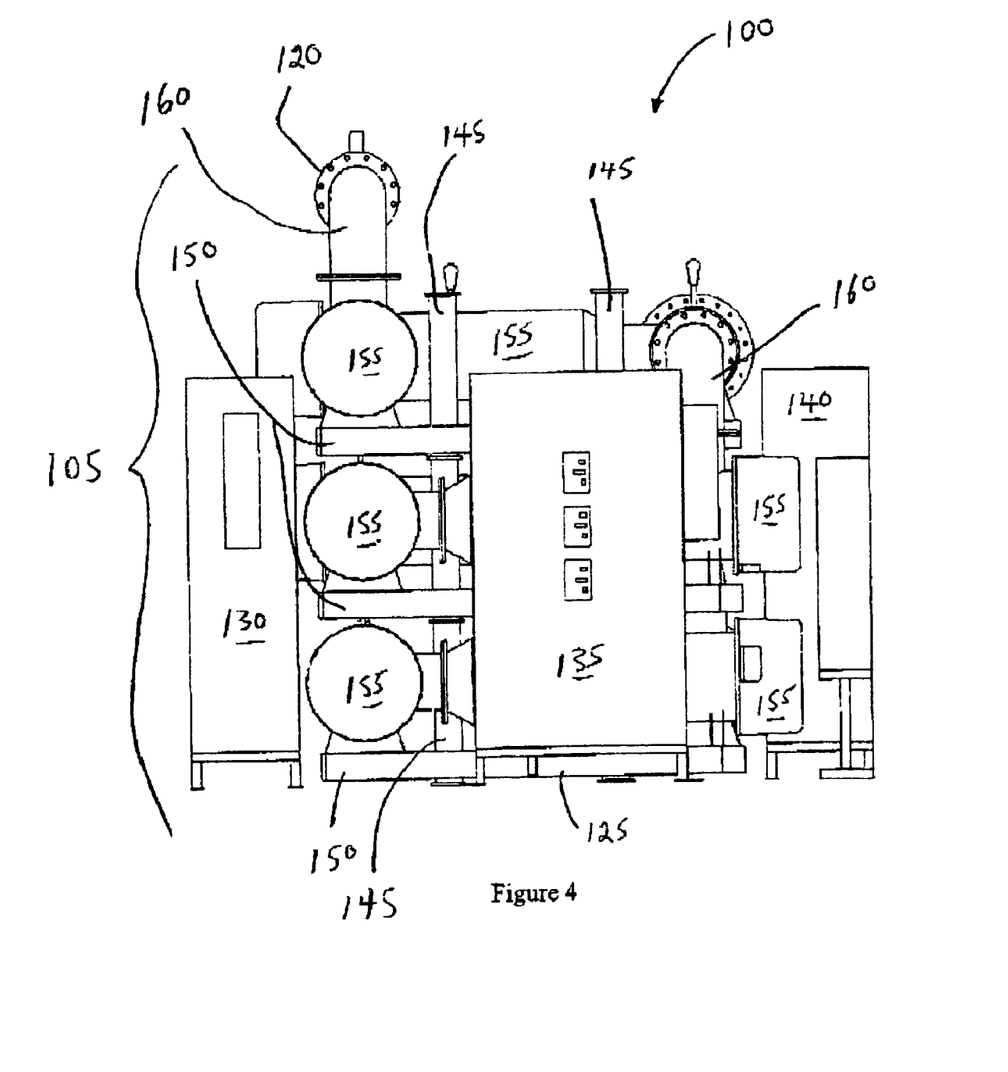
FIG. 4 illustrates a second side elevation of the system illustrated in FIG. 1.
Figure 5:
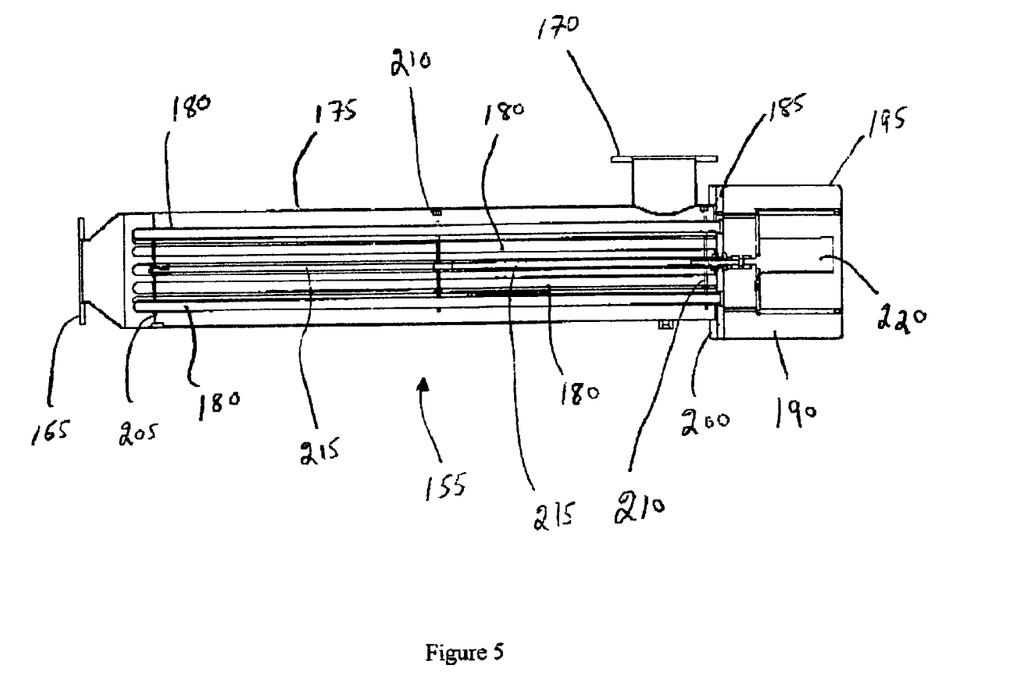
FIG. 5 illustrates a section of one reactor used in the system illustrated in FIGS. 1–4.

With reference to FIG. 5, radiation reactor 155 comprises a reactor inlet 165 and a reactor outlet 170. Reactor inlet 165 and reactor outlet 170 are interconnected by a substantially tubular housing 175. Tubular housing 175 has disposed therein a series of elongate tubes 180. Tubes 180 are made from a radiation transparent material such as, for example, quartz.

As illustrated, one end of each tube 180 is closed while the other end is sealingly engaged to a plate 185. The manner of achieving engagements between tubes 180 and plate 185 is conventional and within the purview of a person skilled in the art. Disposed within each tube 180 is a radiation source (not shown for clarity). Preferably, the radiation source is an ultraviolet radiation source. The nature of the ultraviolet radiation source is not particularly restricted. In one embodiment, the ultraviolet radiation source may be low-pressure ultraviolet radiation lamp. In another embodiment, the ultraviolet radiation source may be a medium pressure lamp. In yet another embodiment, the ultraviolet radiation source may be a low-pressure amalgam lamp. In yet another embodiment, the ultraviolet radiation source may be a low-pressure, high-output (LPHO) lamp. Such lamps are commercially available and are known in the art. As is known in the art, the radiation source typically comprises electrical leads (again not shown for clarity) which, in this case, would emanate from the open end of tubes 180 to a supplementary housing 190 defined by an end cap 195 attached to a flange 200 of tubular housing 175.

Disposed within tubular housing 175 is a support plate 205 which serves to support each elongate tube 180 near the closed end thereof.

Also disposed within tubular housing 175 are a pair of cleaning yokes 210. Cleaning yokes 210 are attached to a screw drive 215. Screw drive 215 is attached to a drive motor 220 which is disposed in supplementary housing 190.

Preferably, cleaning yokes 210 comprise mechanical scrapers. For example, it is possible for cleaning yokes 210 to comprise a cleaning ring per elongate sleeve. Preferably, the cleaning ring comprises an O-ring which surrounds elongate tubes 180. The O-ring would scrape fouling materials from the exterior of elongate tubes 180 as cleaning yokes 210 are moved along the tubes by screw drive 215. Of course, other cleaning systems may be attached to screw drive 215 such as chemical-mechanical cleaning systems (e.g., similar in design and operation to that described in the 896 patent referred to above).

The number of elongate tubes 180 disposed within tubular housing 175 is not particularly restricted. For example, the number of tubes (and thus the number of radiation sources or lamps) disposed within each reactor 155 may be from 3 to 72. Each reactor in the array may be substantially identical, or the reactors in the array may be non-identical.

The operation of fluid treatment system 100 will now be described.

Water which is in need of disinfection enters fluid treatment system 100 at inlet 115. Inlet 115 is connected to reactor inlet 165 of one reactor 155. Water then enters that specific reactor 155 and is treated by radiation emanating from elongate tubes 180. The treated water then exits that reactor 155 via the outlet 170 and enters the next reactor 155. This sequence of events repeats itself until the fluid had been passed through all nine reactors after which it exits fluid treatment system 100 via outlet 120. As will be appreciated by those of skill in the art, in the illustrated embodiment, the fluid travels in a generally helical fashion through fluid treatment reactor array 105. As will be further appreciated by those of skill in the art, reactor 155 is simply a repeating unit which can be used in fluid treatment reactor array 105 with minimal additional pieces (e.g., elbows 160 and straight sections which interconnect the system inlet/outlet to the nearest reactor 155.

A distinct advantage of the present fluid treatment system is that a large volume of fluid can be treated since the fluid is passing through a series of 9 reactors. Further advantage of course is that this can be achieved using a very small footprint for the fluid treatment reactor array.

It will be apparent to those of skill in the art that variations to the specific design shown in FIGS. 1–5 can be made without departing from the spirit and scope of the present invention. For example, it is possible to modify, replace or supplement elbows 160 with one or more T-shaped sections, each T-shaped section comprising suitable valving or the like, which allow for diversion (e.g., by means of supplementary piping, hoses or the like) of fluid flow from a portion of fluid treatment reactor array 105 while leaving the remaining portion of array 105 operational. This can be advantageous to do maintenance on a portion of the array without having to shut down the entire system or to conserve energy if the transmittance of the water being treated increases. Further, it is possible to modify the illustrated embodiment to increase the number of rows of reactors in the fluid treatment reactor array and/or to increase the number of reactors in each row in the array. Still further, while the illustrated embodiment shows a control panel (typically containing a programmable logic controller) remote from fluid treatment reactor array 105, it is, of course, possible to modify the illustrated embodiment to incorporate the function of control panel 110 in one or more of power control panels 130,135,140.

The diameter of tubular housing 175 is not particularly restricted. Preferred diameters are within the range from about 6 inches to about 40 inches (particularly preferred diameters are 8 inches, 12 inches, 16 inches, 20 inches, 24 inches, 30 inches and 40 inches).

In the illustrated embodiment, the inlet to each reactor 155 is oriented such that the direction of fluid flow is substantially parallel to elongate tubes 180 whereas the orientation of reactor outlet 170 is such that the flow of fluid therethrough is substantially transverse perpendicular to the longitudinal axis of elongate tubes 180. While this is a highly preferred orientation of reactor inlet 165 and reactor outlet 170 in relation to the direction of fluid flow and longitudinal axis of elongate tubes 180, it is possible to modify these specific features of reactor 155. For example, the longitudinal axis of the elongate radiation source may be substantially parallel to the direction of fluid flow through the fluid treatment zone, it may be substantially transverse to the direction of fluid flow through the fluid treatment zone, or it may be substantially orthogonal to the direction of fluid flow through the fluid treatment zone.

A further distinct advantage of the present fluid treatment system is that the rows of reactors used in fluid treatment reactor array can be modularized. This facilitates shipping and construction of the system and also facilitates expansion or reduction of system capacity in the future. For example, with respect to the illustrated embodiment, it will be seen that vertical supports 145 comprise flange plate elements surrounding each row of reactors 155. This allows for modulization of rows of reactors 155 and the advantages associated therewith.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each, individual publication, patent or patent application was specifically and individually indicated to be incorporated by reference in its entirety.

What is claimed is:

1. A fluid treatment system comprising:
an array of independent fluid treatment reactors arranged in a manner whereby a flow of fluid may be passed through the array in a substantially helical direction, each reactor comprising:
a reactor inlet;
a reactor outlet;
a housing between the reactor inlet and the reactor outlet; and
a fluid treatment zone disposed in the housing, the fluid treatment zone comprising a plurality of elongate radiation sources, each elongate radiation source having a longitudinal axis.

2. The system defined in claim 1, wherein each reactor in the array is substantially identical.

3. The system defined in claim 1, wherein reactors in the array are non-identical.

4. The system defined in claim 1, wherein the array comprises a plurality of rows of reactors, each row comprising a plurality of reactors.

5. The system defined in claim 1, wherein the housing comprises an elongate tubular housing.

6. A fluid treatment system comprising:
an array of independent fluid treatment reactors arranged in a manner whereby a flow of fluid may be passed through the array in a substantially helical direction, each reactor comprising:
a reactor inlet;
a reactor outlet;
a housing between the reactor inlet and the reactor outlet; and
a fluid treatment zone disposed in the housing, the fluid treatment zone comprising a plurality of elongate radiation sources, each elongate radiation source having a longitudinal axis, wherein the longitudinal axis of at least one elongate radiation source is substantially parallel to a direction of fluid flow through the fluid treatment zone.

7. A fluid treatment system comprising:
an array of independent fluid treatment reactors arranged in a manner whereby a flow of fluid may be passed through the array in a substantially helical direction, each reactor comprising:
a reactor inlet;
a reactor outlet;
a housing between the reactor inlet and the reactor outlet; and
a fluid treatment zone disposed in the housing, the fluid treatment zone comprising a plurality of elongate radiation sources, each elongate radiation source having a longitudinal axis, wherein the longitudinal axis of the elongate radiation source is substantially transverse to a direction of fluid flow through the fluid treatment zone.

8. The system defined in claim 1, wherein the longitudinal axis of the elongate radiation source is substantially orthogonal to a direction of fluid flow through the fluid treatment zone.

9. A fluid treatment system comprising:
an array of independent fluid treatment reactors arranged in a manner whereby a flow of fluid may be passed through the array in a substantially helical direction, each reactor comprising:
a reactor inlet;
a reactor outlet;
an elongate housing between the reactor inlet and the reactor outlet; and
a fluid treatment zone disposed in the housing, the fluid treatment zone comprising a plurality of elongate radiation sources, each elongate radiation source having a longitudinal axis, wherein the reactor inlet is oriented so that a direction of fluid flow therethrough is substantially parallel to the longitudinal axis of the elongate housing.

10. A fluid treatment system comprising:
an array of independent fluid treatment reactors arranged in a manner whereby a flow of fluid may be passed through the array in a substantially helical direction, each reactor comprising:
a reactor inlet;
a reactor outlet;
an elongate housing between the reactor inlet and the reactor outlet; and
a fluid treatment zone disposed in the housing, the fluid treatment zone comprising a plurality of elongate radiation sources, each elongate radiation source having a longitudinal axis, wherein the reactor outlet is oriented such that a direction of fluid flow therethrough is substantially transverse to the longitudinal axis of the elongate housing.

11. The system defined in claim 1, wherein the fluid treatment zone further comprises a cleaning system for removing fouling materials from the radiation sources.

12. The system defined in claim 1, wherein each reactor comprises an elongate treatment zone.

13. A fluid treatment system comprising:
an array of independent fluid treatment reactors arranged in a manner whereby a flow of fluid may be passed through the array in a substantially helical direction, wherein the array comprises at least two interconnected rows of reactors, each row of reactors comprising at least two interconnected reactors, the rows of reactors being substantially stacked.

14. A fluid treatment system comprising:
an array of independent fluid treatment reactors arranged in a manner whereby a flow of fluid may be passed through the array in a substantially helical direction, wherein the array comprises a plurality of rows of reactors arranged in a helical pattern, each row in the helical pattern comprising at least 3 reactors, per row of the helical pattern.

15. A fluid treatment system comprising:
an array of independent fluid treatment reactors arranged in a manner whereby a flow of fluid may be passed through the array in a substantially helical direction, wherein the array comprises a plurality of rows of reactors arranged in a helical pattern, each row in the helical pattern comprising from 3 to 6 reactors, per row of the helical pattern.

16. A fluid treatment system comprising:
an array of independent fluid treatment reactors arranged in a manner whereby a flow of fluid may be passed through the array in a substantially helical direction, wherein the array comprises a plurality of rows of reactors interconnected to define a substantially helical pathway for fluid to flow therethrough.

17. The system defined in claim 16, wherein the array comprises from 2 to 10 rows of interconnected reactors.

18. A method of treating fluid comprising the steps of:
providing an array of independent fluid treatment reactors arranged in a substantially helical direction and such that each reactor has: (i) a reactor inlet; (ii) a reactor outlet; (iii) a housing between the reactor inlet and the reactor outlet; and (iv) a fluid treatment zone disposed in the housing, the fluid treatment zone comprising a plurality of elongate radiation sources, each elongate radiation source having a longitudinal axis; and
feeding fluid to be treated through the array of independent fluid treatment reactors in a substantially helical direction.

19. The system defined in claim 6, wherein each reactor in the array is substantially identical.

20. The system defined in claim 6, wherein reactors in the array are non-identical.

21. The system defined in claim 6, wherein the array comprises a plurality of rows of reactors, each row comprising a plurality of reactors.

22. The system defined in claim 6, wherein the reactor inlet is oriented so that a direction of fluid flow therethrough is substantially parallel to the longitudinal axis of the housing.

23. The system defined in claim 6, wherein the reactor outlet is oriented such that a direction of fluid flow therethrough is substantially transverse to the longitudinal axis of the housing.

24. The system defined in claim 6, wherein the fluid treatment zone further comprises a cleaning system for removing fouling materials from the radiation sources.

25. The system defined in claim 6, wherein each reactor comprises an elongate treatment zone.

26. The system defined in claim 6, wherein the array comprises at least two interconnected rows of reactors, each row of reactors comprising at least two interconnected reactors, the rows of reactors being substantially stacked.

27. The system defined in claim 6, wherein the array comprises a plurality of rows of reactors arranged in a helical pattern, each row in the helical pattern comprising at least 3 reactors, per row of the helical pattern.

28. The system defined in claim 6, wherein the array comprises a plurality of rows of reactors arranged in a helical pattern, each row in the helical pattern comprising from 3 to 6 reactors, per row of the helical pattern.

29. The system defined in claim 6, wherein the array comprises a plurality of rows of reactors interconnected to define a substantially helical pathway for fluid to flow therethrough.

30. The system defined in claim 29, wherein the array comprises from 2 to 10 rows of interconnected reactors.

31. The system defined in claim 7, wherein each reactor in the array is substantially identical.

32. The system defined in claim 7, wherein reactors in the array are non-identical.

33. The system defined in claim 7, wherein the array comprises a plurality of rows of reactors, each row comprising a plurality of reactors.

34. The system defined in claim 7, wherein the reactor inlet is oriented so that a direction of fluid flow therethrough is substantially parallel to the longitudinal axis of the housing.

35. The system defined in claim 7, wherein the reactor outlet is oriented such that a direction of fluid flow therethrough is substantially transverse to the longitudinal axis of the housing.

36. The system defined in claim 7, wherein the fluid treatment zone further comprises a cleaning system for removing fouling materials from the radiation sources.

37. The system defined in claim 7, wherein each reactor comprises an elongate treatment zone.

38. The system defined in claim 7, wherein the array comprises at least two interconnected rows of reactors, each row of reactors comprising at least two interconnected reactors, the rows of reactors being substantially stacked.

39. The system defined in claim 7, wherein the array comprises a plurality of rows of reactors arranged in a helical pattern, each row in the helical pattern comprising at least 3 reactors, per row of the helical pattern.

40. The system defined in claim 7, wherein the array comprises a plurality of rows of reactors arranged in a helical pattern, each row in the helical pattern comprising from 3 to 6 reactors, per row of the helical pattern.

41. The system defined in claim 7, wherein the array comprises a plurality of rows of reactors interconnected to define a substantially helical pathway for fluid to flow therethrough.

42. The system defined in claim 40, wherein the array comprises from 2 to 10 rows of interconnected reactors.

43. The system defined in claim 9, wherein each reactor in the array is substantially identical.

44. The system defined in claim 9, wherein reactors in the array are non-identical.

45. The system defined in claim 9, wherein the array comprises a plurality of rows of reactors, each row comprising a plurality of reactors.

46. The system defined in claim 9, wherein the longitudinal axis of at least one elongate radiation source is substantially parallel to a direction of fluid flow through the fluid treatment zone.

47. The system defined in claim 9, wherein the longitudinal axis of at least one elongate radiation source is substantially transverse to a direction of fluid flow through the fluid treatment zone.

48. The system defined in claim 9, wherein the fluid treatment zone further comprises a cleaning system for removing fouling materials from the radiation sources.

49. The system defined in claim 9, wherein each reactor comprises an elongate treatment zone.

50. The system defined in claim 9, wherein the array comprises at least two interconnected rows of reactors, each row of reactors comprising at least two interconnected reactors, the rows of reactors being substantially stacked.

51. The system defined in claim 9, wherein the array comprises a plurality of rows of reactors arranged in a helical pattern, each row in the helical pattern comprising at least 3 reactors, per row of the helical pattern.

52. The system defined in claim 9, wherein the array comprises a plurality of rows of reactors arranged in a helical pattern, each row in the helical pattern comprising from 3 to 6 reactors, per row of the helical pattern.

53. The system defined in claim 9, wherein the array comprises a plurality of rows of reactors interconnected to define a substantially helical pathway for fluid to flow therethrough.

54. The system defined in claim 53, wherein the array comprises from 2 to 10 rows of interconnected reactors.

55. The system defined in claim 10, wherein each reactor in the array is substantially identical.

56. The system defined in claim 10, wherein reactors in the array are non-identical.

57. The system defined in claim 10, wherein the array comprises a plurality of rows of reactors, each row comprising a plurality of reactors.

58. The system defined in claim 10, wherein the longitudinal axis of at least one elongate radiation source is substantially parallel to a direction of fluid flow through the fluid treatment zone.

59. The system defined in claim 10, wherein the longitudinal axis of at least one elongate radiation source is substantially transverse to a direction of fluid flow through the fluid treatment zone.

60. The system defined in claim 10, wherein the fluid treatment zone further comprises a cleaning system for removing fouling materials from the radiation sources.

61. The system defined in claim 10, wherein each reactor comprises an elongate treatment zone.

62. The system defined in claim 10, wherein the array comprises at least two interconnected rows of reactors, each row of reactors comprising at least two interconnected reactors, the rows of reactors being substantially stacked.

63. The system defined in claim 10, wherein the array comprises a plurality of rows of reactors arranged in a helical pattern, each row in the helical pattern comprising at least 3 reactors, per row of the helical pattern.

64. The system defined in claim 10, wherein the array comprises a plurality of rows of reactors arranged in a helical pattern, each row in the helical pattern comprising from 3 to 6 reactors, per row of the helical pattern.

65. The system defined in claim 10, wherein the array comprises a plurality of rows of reactors interconnected to define a substantially helical pathway for fluid to flow therethrough.

66. The system defined in claim 65, wherein the array comprises from 2 to 10 rows of interconnected reactors.

67. The system defined in claim 13, wherein each reactor in the array is substantially identical.

68. The system defined in claim 13, wherein reactors in the array are non-identical.

69. The system defined in claim 13, wherein each reactor comprises a reactor inlet, a reactor outlet, an elongate tubular housing between the reactor inlet and the reactor outlet, and a fluid treatment zone disposed in the elongate housing.

70. The system defined in claim 69, wherein the fluid treatment zone comprises a plurality of elongate radiation sources, each elongate radiation source having a longitudinal axis.

71. The system defined in claim 70, wherein the longitudinal axis of the elongate radiation source is substantially parallel to a direction of fluid flow through the fluid treatment zone.

72. The system defined in claim 70, wherein the longitudinal axis of the elongate radiation source is substantially transverse to a direction of fluid flow through the fluid treatment zone.

73. The system defined in claim 69, wherein the reactor inlet is oriented so that a direction of fluid flow therethrough is substantially parallel to the longitudinal axis of the elongate housing.

74. The system defined in claim 69, wherein the reactor outlet is oriented such that a direction of fluid flow therethrough is substantially transverse to the longitudinal axis of the elongate housing.

75. The system defined in claim 69, wherein the fluid treatment zone further comprises a cleaning system for removing fouling materials from the radiation sources.

76. The system defined in claim 69, wherein each reactor comprises an elongate treatment zone.

77. The system defined in claim 13, wherein the array comprises a plurality of rows of reactors arranged in a helical pattern, each row in the helical pattern comprising at least 3 reactors, per row of the helical pattern.

78. The system defined in claim 13, wherein the array comprises a plurality of rows of reactors arranged in a helical pattern, each row in the helical pattern comprising from 3 to 6 reactors, per row of the helical pattern.

79. The system defined in claim 13, wherein the array comprises from 2 to 9 rows of interconnected reactors.

80. The system defined in claim 14, wherein each reactor in the array is substantially identical.

81. The system defined in claim 14, wherein reactors in the array are non-identical.

82. The system defined in claim 14, wherein each reactor comprises a reactor inlet, a reactor outlet, an elongate tubular housing between the reactor inlet and the reactor outlet, and a fluid treatment zone disposed in the elongate housing.

83. The system defined in claim 82, wherein the fluid treatment zone comprises a plurality of elongate radiation sources, each elongate radiation source having a longitudinal axis.

84. The system defined in claim 83, wherein the longitudinal axis of the elongate radiation source is substantially parallel to a direction of fluid flow through the fluid treatment zone.

85. The system defined in claim 83, wherein the longitudinal axis of the elongate radiation source is substantially transverse to a direction of fluid flow through the fluid treatment zone.

86. The system defined in claim 82, wherein the reactor inlet is oriented so that a direction of fluid flow therethrough is substantially parallel to the longitudinal axis of the elongate housing.

87. The system defined in claim 82, wherein the reactor outlet is oriented such that a direction of fluid flow therethrough is substantially transverse to the longitudinal axis of the elongate housing.

88. The system defined in claim 82, wherein the fluid treatment zone further comprises a cleaning system for removing fouling materials from the radiation sources.

89. The system defined in claim 82, wherein each reactor comprises an elongate treatment zone.

90. The system defined in claim 14, wherein the array comprises a plurality of rows of reactors arranged in a helical pattern, each row in the helical pattern comprising from 3 to 6 reactors, per row of the helical pattern.

91. The system defined in claim 14, wherein the array comprises from 2 to 10 rows of interconnected reactors.

92. The system defined in claim 15, wherein each reactor in the array is substantially identical.

93. The system defined in claim 15, wherein reactors in the array are non-identical.

94. The system defined in claim 15, wherein each reactor comprises a reactor inlet, a reactor outlet, an elongate tubular housing between the reactor inlet and the reactor outlet, and a fluid treatment zone disposed in the elongate housing.

95. The system defined in claim 94, wherein the fluid treatment zone comprises a plurality of elongate radiation sources, each elongate radiation source having a longitudinal axis.

96. The system defined in claim 95, wherein the longitudinal axis of the elongate radiation source is substantially parallel to a direction of fluid flow through the fluid treatment zone.

97. The system defined in claim 95, wherein the longitudinal axis of the elongate radiation source is substantially transverse to a direction of fluid flow through the fluid treatment zone.

98. The system defined in claim 94, wherein the reactor inlet is oriented so that a direction of fluid flow therethrough is substantially parallel to the longitudinal axis of the elongate housing.

99. The system defined in claim 94, wherein the reactor outlet is oriented such that a direction of fluid flow therethrough is substantially transverse to the longitudinal axis of the elongate housing.

100. The system defined in claim 94, wherein the fluid treatment zone further comprises a cleaning system for removing fouling materials from the radiation sources.

101. The system defined in claim 94, wherein each reactor comprises an elongate treatment zone.

102. The system defined in claim 15, wherein the array comprises from 2 to 10 rows of interconnected reactors.

103. The system defined in claim 16, wherein each reactor in the array is substantially identical.

104. The system defined in claim 16, wherein reactors in the array are non-identical.

105. The system defined in claim 16, wherein the array comprises a plurality of rows of reactors, each row comprising a plurality of reactors.

106. The system defined in claim 16, wherein each reactor comprises a reactor inlet, a reactor outlet, an elongate tubular housing between the reactor inlet and the reactor outlet, and a fluid treatment zone disposed in the elongate housing.

107. The system defined in claim 106, wherein the fluid treatment zone comprises a plurality of elongate radiation sources, each elongate radiation source having a longitudinal axis.

108. The system defined in claim 107, wherein the longitudinal axis of the elongate radiation source is substantially parallel to a direction of fluid flow through the fluid treatment zone.

109. The system defined in claim 107, wherein the longitudinal axis of the elongate radiation source is substantially transverse to a direction of fluid flow through the fluid treatment zone.

110. The system defined in claim 106, wherein the reactor inlet is oriented so that a direction of fluid flow therethrough is substantially parallel to the longitudinal axis of the elongate housing.

111. The system defined in claim 106, wherein the reactor outlet is oriented such that a direction of fluid flow therethrough is substantially transverse to the longitudinal axis of the elongate housing.

112. The system defined in claim 106, wherein the fluid treatment zone further comprises a cleaning system for removing fouling materials from the radiation sources.

113. The system defined in claim 106, wherein each reactor comprises an elongate treatment zone.

114. The system defined in claim 16, wherein the array comprises at least two interconnected rows of reactors, each row of reactors comprising at least two interconnected reactors, the rows of reactors being substantially stacked.

115. The system defined in claim 16, wherein the array comprises a plurality of rows of reactors arranged in a helical pattern, each row in the helical pattern comprising 3 reactors, per row of the helical pattern.

116. The system defined in claim 16, wherein the array comprises a plurality of rows of reactors arranged in a helical pattern, each row in the helical pattern comprising from 3 to 6 reactors, per row of the helical pattern.

117. The method defined in claim 18, wherein the array comprises from 2 to 10 rows of interconnected reactors.

* * * * *